(12) United States Patent
Kim et al.

(10) Patent No.: US 10,591,211 B2
(45) Date of Patent: Mar. 17, 2020

(54) WASHSTAND FURNITURE

(71) Applicant: LG ELECTRONICS INC., Seoul (KR)

(72) Inventors: Jongseok Kim, Seoul (KR); Seongho Kim, Seoul (KR); Ungje Jo, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 15/915,193

(22) Filed: Mar. 8, 2018

(65) Prior Publication Data

US 2018/0259254 A1 Sep. 13, 2018

(30) Foreign Application Priority Data

Mar. 8, 2017 (KR) ........................ 10-2017-0029728

(51) Int. Cl.
| | | |
|---|---|---|
| *F26B 9/00* | (2006.01) | |
| *A47K 1/02* | (2006.01) | |
| *E03C 1/04* | (2006.01) | |
| *A61L 2/10* | (2006.01) | |
| *F26B 9/06* | (2006.01) | |
| *F26B 3/04* | (2006.01) | |
| *E03C 1/32* | (2006.01) | |
| *E03C 1/14* | (2006.01) | |

(52) U.S. Cl.
CPC ............... *F26B 9/066* (2013.01); *A47K 1/02* (2013.01); *A61L 2/10* (2013.01); *E03C 1/04* (2013.01); *F26B 3/04* (2013.01); *A61L 2202/17* (2013.01); *E03C 1/14* (2013.01); *E03C 1/32* (2013.01)

(58) Field of Classification Search
CPC .................................. A47K 1/02; F26B 9/066
USPC .............................................. 134/57 D, 58 D
See application file for complete search history.

(56) References Cited

U.S. PATENT DOCUMENTS

| | | | |
|---|---|---|---|
| 2,175,329 A | 10/1939 | Watt | |
| 2,287,657 A | 6/1942 | Wisckol | |
| 4,146,405 A * | 3/1979 | Timmer | ................. A47L 15/23 |
| | | | 134/115 R |
| 5,522,411 A | 6/1996 | Johnson | |
| (Continued) | | | |

OTHER PUBLICATIONS

U.S. Office Action dated Oct. 5, 2018 issued in related co-pending U.S. Appl. No. 15/915,216.

(Continued)

*Primary Examiner* — Janie M Loeppke
(74) *Attorney, Agent, or Firm* — KED & Associates, LLP

(57) ABSTRACT

There is provided a washstand which may include a washing device that includes a bowl, a water-supply assembly that supplies water to the bowl, and a water-discharge assembly that drains water from the bowl, an inner cabinet provided below the bowl and having an inner space, a dryer configured to draw air through an air-intake hole opened toward a floor and to discharge air into the inner space of the inner cabinet, a utensil drying functional-module provided in the inner space of the inner cabinet and configured to dry utensils using air discharged from the dryer; and an outer cabinet covering an outer side of the inner cabinet. An external connection path may be defined between the inner cabinet and the outer cabinet, wherein the external connection path guides air discharged from the utensil drying functional-module toward the floor.

18 Claims, 12 Drawing Sheets

(56) References Cited

U.S. PATENT DOCUMENTS

| | | |
|---|---|---|
| 5,702,115 A | 12/1997 | Pool |
| 5,727,579 A * | 3/1998 | Chardack ............. A47K 10/485 |
| | | 134/102.3 |
| 5,934,298 A * | 8/1999 | Singh .................. A47L 15/0086 |
| | | 134/115 R |
| 6,802,578 B1 | 10/2004 | Lang et al. |
| 8,245,414 B2 | 8/2012 | Watson |
| 8,283,812 B2 | 10/2012 | Azancot |
| 8,991,067 B2 | 3/2015 | Zielinski |
| 9,255,733 B2 | 2/2016 | Bagwell |
| 9,887,562 B2 | 2/2018 | Racenet et al. |
| 10,317,137 B2 | 6/2019 | Kim et al. |
| 2007/0151302 A1 | 7/2007 | Kendall et al. |
| 2007/0157378 A1 | 7/2007 | Kendall et al. |
| 2008/0256826 A1 | 10/2008 | Zarembinski |
| 2014/0366262 A1 | 12/2014 | Flynn |
| 2015/0252515 A1 | 9/2015 | Henry et al. |
| 2016/0128528 A1 | 5/2016 | Stewen et al. |

OTHER PUBLICATIONS

U.S. Notice of Allowance dated Oct. 19, 2018 issued in co-pending U.S. Appl. No. 15/915,236.
U.S. Office Action dated Aug. 30, 2019 issued in co-pending U.S. Appl. No. 15/915,480.
U.S. Office Action dated Sep. 13, 2019 issued in co-pending U.S. Appl. No. 15/915,332.
U.S. Office Action dated Oct. 2, 2019 issued in U.S. Appl. No. 15/915,401.

* cited by examiner

WASHSTAND FURNITURE

CROSS-REFERENCE TO RELATED APPLICATION(S)

This application claims the benefit of Korean patent application No. 10-2017-0029728, filed in Korea on Mar. 8, 2017, the entire content of which is incorporated herein by reference for all purposes as if fully set forth herein.

U.S. application Ser. Nos. 15/915,193; 15/915,364; 15/915,267; 15/915,332; 15/915,401; 15/915,480; 15/915,421; 15/915,216; 15/915,236, all filed on Mar. 8, 2018, are related and are hereby incorporated by reference in their entirety. Further, one of ordinary skill in the art will recognize that features disclosed in these above-noted applications may be combined in any combination with features disclosed herein.

BACKGROUND

1. Field

Embodiments of the present disclosure relate to a washstand furniture utilizing a space under a washstand, and more particularly to washstand furniture containing a functional functional-module therein.

2. Background

Washstand furniture including functional modules are known. However, they suffer from various disadvantages.

BRIEF DESCRIPTION OF THE DRAWINGS

Embodiments will be described in detail with reference to the following drawings in which like reference numerals refer to like elements, and wherein.

DETAILED DESCRIPTION

For simplicity and clarity of illustration, elements in the figures are not necessarily drawn to scale. The same reference numbers in different figures denote the same or similar elements, and as such perform similar functionality. Also, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

In general, utensils used in the bathroom may include numerous types of items that may be used in a bathroom. Utensils include those necessary for bathroom activities, such as toilet bowls and shower tools. Utensils used in the bathroom commonly involve exposure to water. Therefore, the utensils used in the bathroom will have moisture left thereon after use.

Bathrooms are mostly humid spaces. Thus, in an inner space of furniture such as cabinets for washstands or sink vanities, fungus or bacteria may easily grow or water particles may deposit to pose potential issues. Thus, utensils used in the bathroom may often be infected with fungus or bacteria.

To prevent this, it is therefore necessary to remove moisture from the utensils used in the bathrooms. One way to remove moisture from the utensil may be to use a dehydrating machine. However, using the dehydrating machine, a subsequent drying process is required. Therefore, perfect moisture removal is hardly expected. The washstand furniture as broadly described and embodied herein addresses these as well as other concerns.

Embodiments of the present disclosure are to provide washstand furniture to be able to dry a utensil used in a bathroom. Embodiments of the present disclosure are to provide washstand furniture to recycle waste heat coming from warm air used in utensil drying process. Embodiments of the present disclosure are to provide washstand furniture that effectively dries an inner portion of a functional-module.

Figure 1:
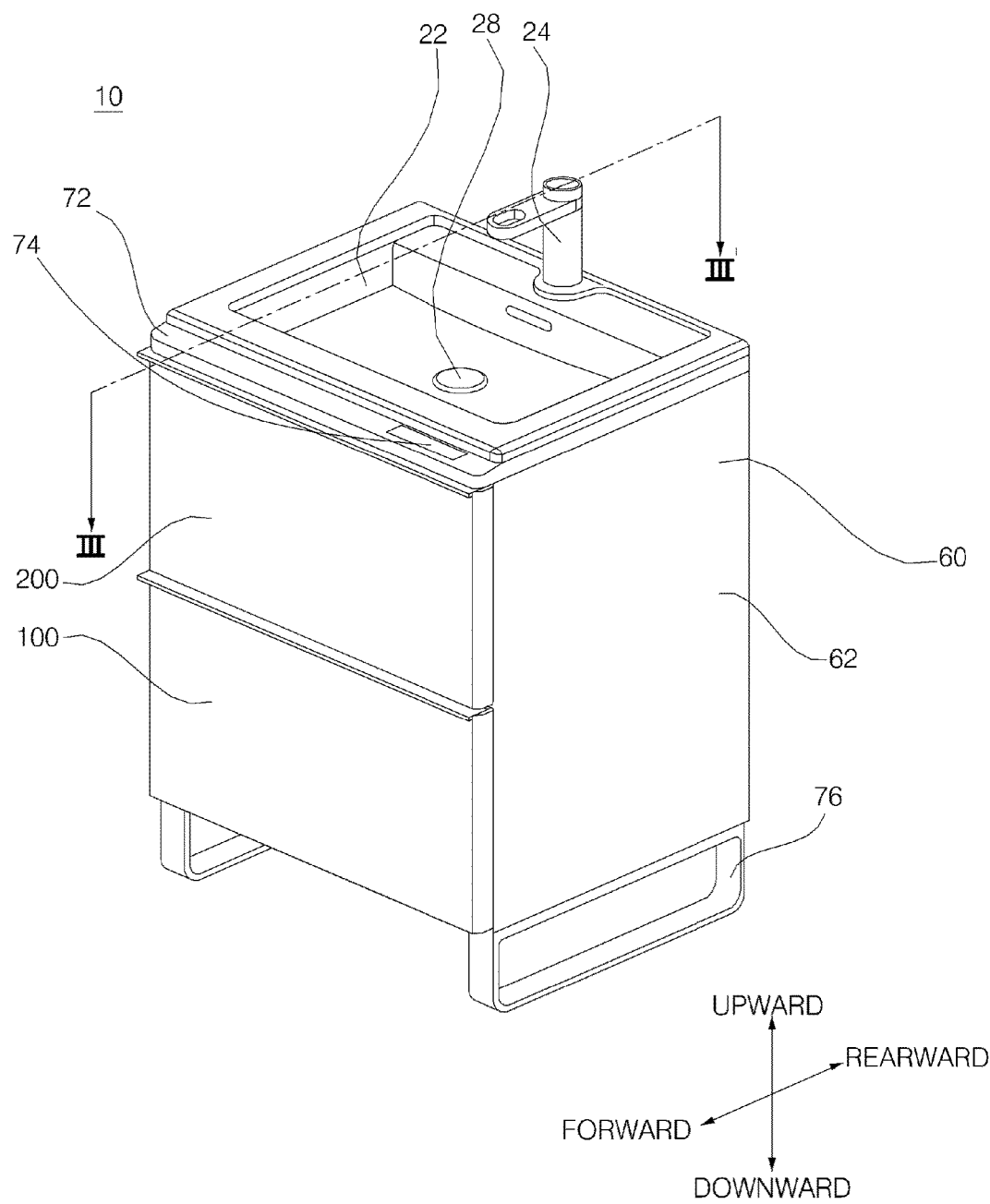
FIG. 1 is a perspective view of washstand furniture according to one embodiment of the present disclosure.
Figure 2:
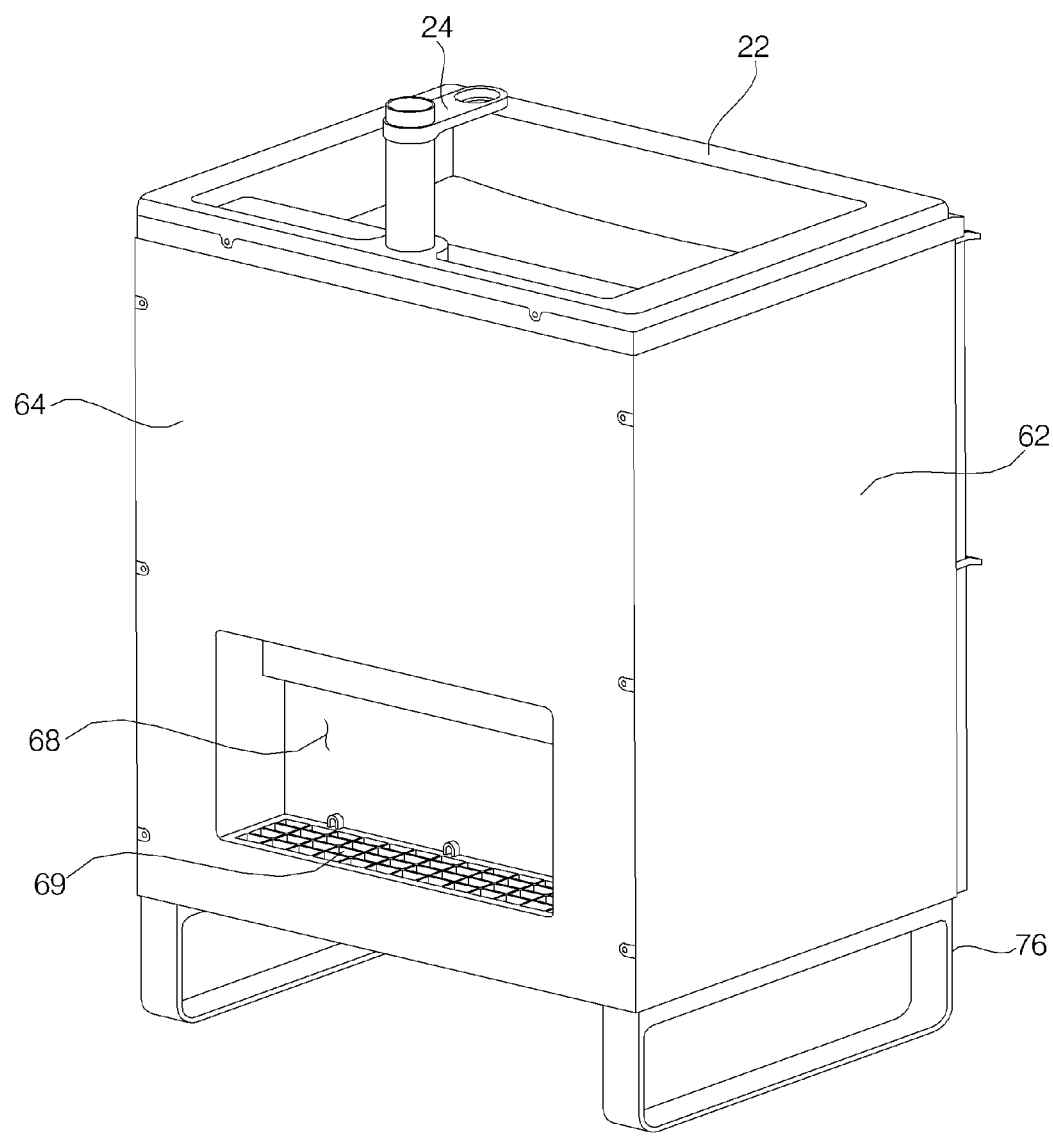
FIG. 2 is a rear face perspective view of washstand furniture according to an embodiment of the present disclosure.
Figure 3:
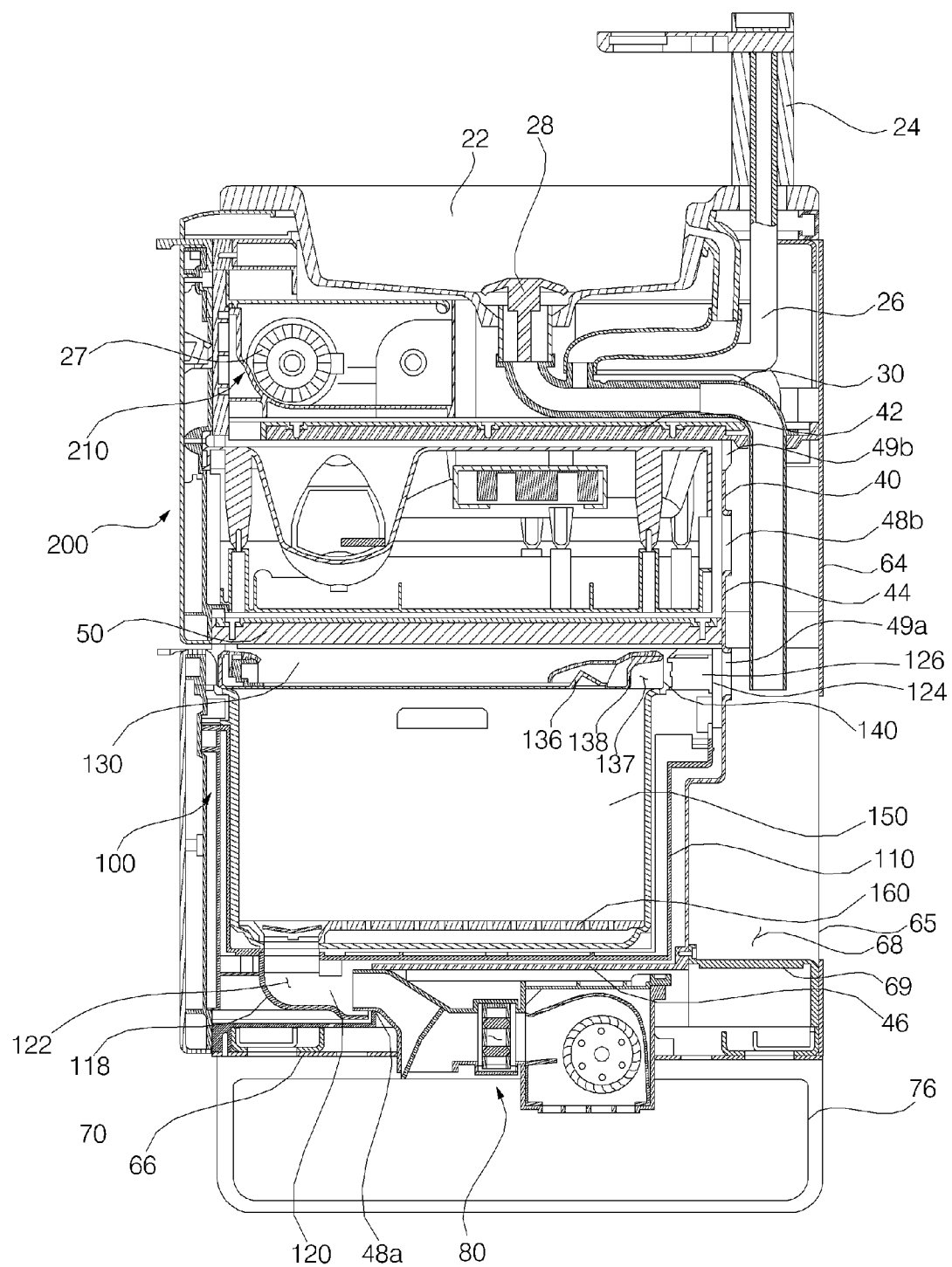
FIG. 3 is a cross-sectional view taken in a line III-III' in FIG. 1.
Figure 4:
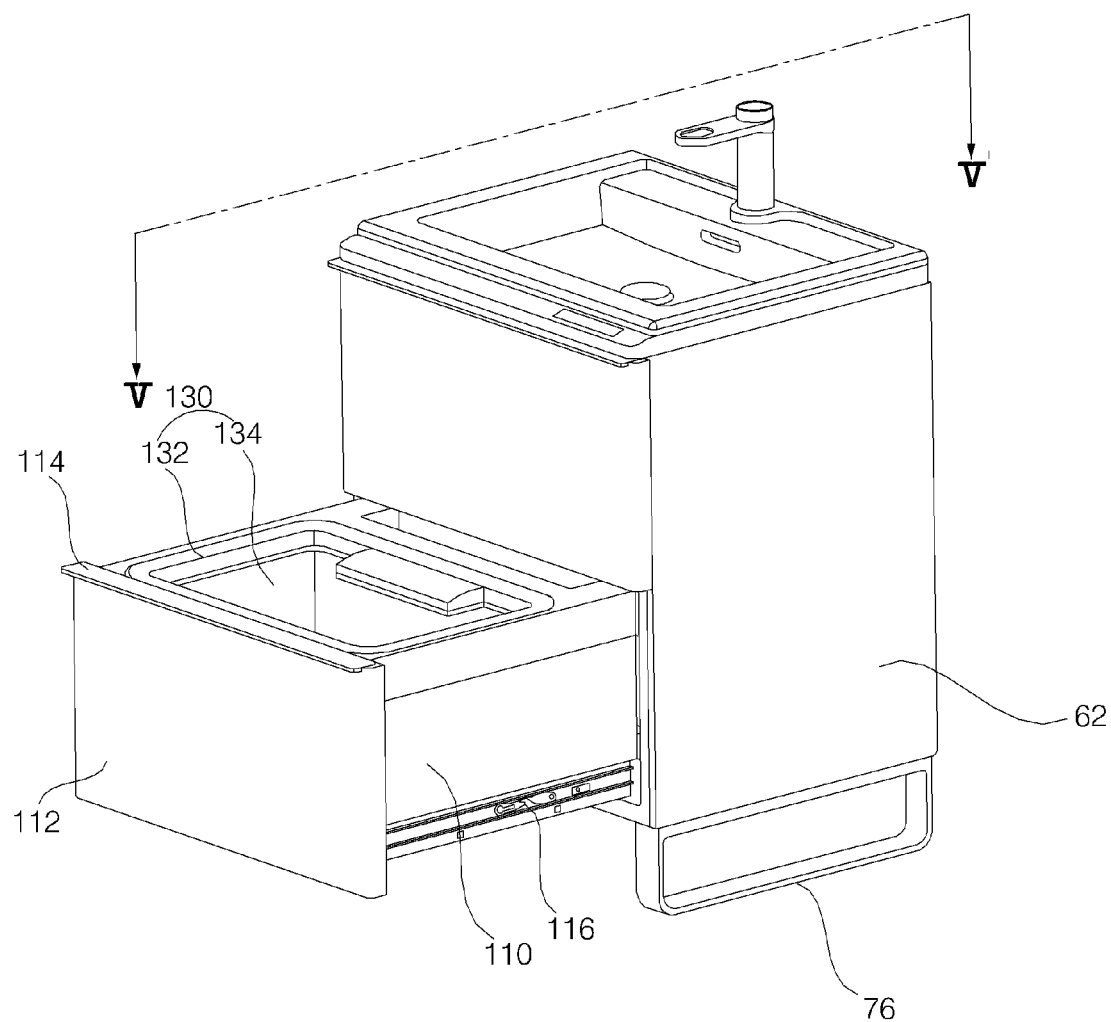
FIG. 4 is a view showing a state in which a first functional-module of washstand furniture according to an embodiment of the present disclosure is taken out.
Figure 5:
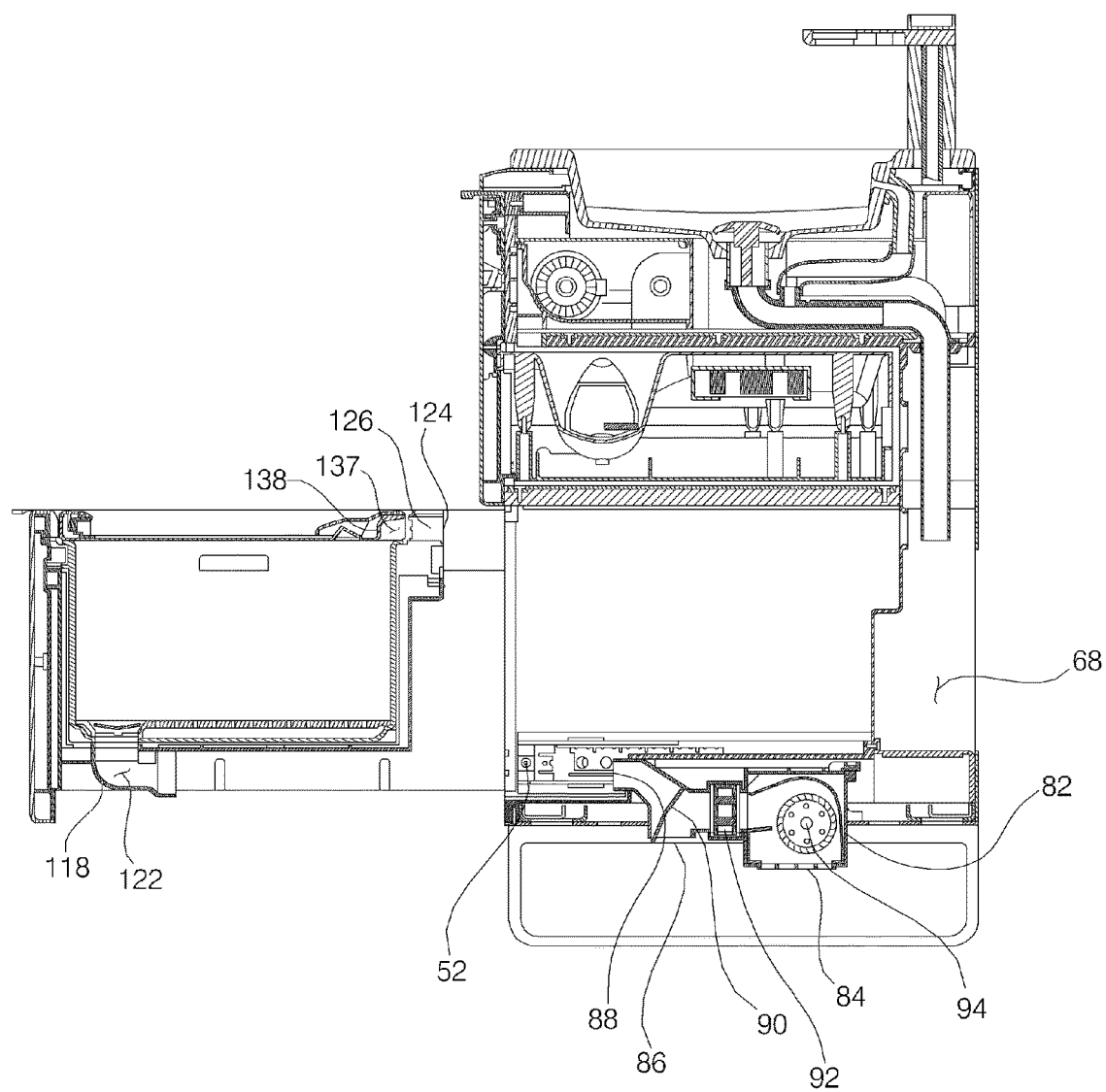
FIG. 5 is a cross-sectional view taken in a line V-V' in FIG. 4.

FIG. 1 is a perspective view of washstand furniture according to one embodiment of the present disclosure. FIG. 2 is a rear face perspective view of washstand furniture according to an embodiment of the present disclosure. FIG. 3 is a cross-sectional view taken in a line III-III' in FIG. 1. FIG. 4 is a view showing a state in which a first functional-module of washstand furniture according to an embodiment of the present disclosure is taken out. FIG. 5 is a cross-sectional view taken in a line V-V' in FIG. 4.

The washstand furniture 10 (or washstand, vanity) may include a washing device including a bowl portion (or bowl, sink, basin), a water-supply assembly for supplying water to the bowl portion; a water-discharge assembly for draining water from the bowl portion; an inner cabinet 40 disposed below the bowl portion and having an interior space defined therein; an air-conditioning device 80 (or dryer) configured to draw air through an air-intake hole opened toward the bathroom floor and to discharge air into the inner space of the inner cabinet; a utensil drying functional-module 100 disposed in the inner space of the inner cabinet and configured to dry the utensils held therein using air discharged from the air-conditioning device; and an outer cabinet 60 covering an outer side of the inner cabinet, wherein an external connection path 68 (or external connection recess/channel) is defined between the inner cabinet and the outer cabinet, wherein the external connection path 68 guides air discharged from the utensil drying functional-module toward the bottom of the bathroom.

With reference to FIG. 1, for describing the washstand furniture according to the present embodiment, a direction in which the functional-module is drawn out to the outside of the cabinet is defined as forward (F), the reverse direction (R) is defined as opposite to the forward direction, and a portion in which the bowl portion is disposed is defined as an upper portion (U), and a portion in which a furniture legs are disposed is defined as a lower portion (L). This is for the purpose of facilitating the description of the disclosure and does not limit the scope of the disclosure.

A washing device is a device that may be installed on the wall of a bathroom or washroom and is designed to allow the user to wash his/her hands, face, etc. The washing device may include the bowl portion 22 for receiving water therein, the water-supply assembly for supplying water to the bowl portion 22, and the water-discharge assembly for draining the water supplied to the bowl portion 22.

The bowl portion 22 may be made of enamel, ceramic, or the like. The bowl portion may be formed of the enamel which allows the bowl portion to be morphologically variously deformable and easy to be coupled with the cabinet. The bowl portion 22 may be disposed at the top portion of the washstand furniture 10.

The water-supply assembly includes a water-supply valve 24 opened and closed to supply water to the bowl portion 22, and a water-supply hose 26 for supplying water to the water-supply valve 24. The water-supply valve 24 is disposed at one side of the bowl portion 22 to control the supply of water to the bowl portion 22. The water-supply hose 26 may include a hot water-supply hose supplying hot water and a cold water-supply hose supplying cold water.

The water-supply assembly may further comprise a water-purification filter 27 for purifying the water entering the water-supply hose 26. The water-purification filter 27 is configured to purify the water to be supplied to the bowl portion 22 through the water-supply valve 24.

The water-discharge assembly includes a water-discharge tube 30 for discharging the water stored in the bowl portion 22 to the outside, and a pop-up valve 28 for storing water in the bowl portion 22 or for sending the filled water to the water-discharge tube 30.

Below the washing device, the cabinet which forms the contour of washstand furniture 10 may be placed. The cabinet maintains the rigidity of the washstand furniture 10 and provides a space for various functional-modules to be installed therein. The cabinet may be hollow and may have an open front.

The cabinet may include an inner cabinet 40 for accommodating a functional-module therein, and an outer cabinet 60 disposed outside the inner cabinet 40 to maintain the rigidity of the cabinet. The washstand furniture 10 may include the inner cabinet 40 in addition to the outer cabinet 60, and thus, the inflow of water into the functional-module housed inside the inner cabinet 40 may be doubly blocked.

The inner cabinet 40 may have a box shape in which the inside is hollow and the front is opened. The outer cabinet 60 may be disposed outside the inner cabinet 40. The outer cabinet 60 may include lateral outer cabinets 62 (or lateral outer cabinet wall) arranged to cover both sides of the inner cabinet 40, a rear outer cabinet 64 (or rear outer cabinet wall) disposed to cover a rear face 44 of the inner cabinet 40, and a base outer cabinet 66 (or base outer cabinet wall) disposed to cover a bottom face 46 of the inner cabinet 40. The rear outer cabinet 64 may have a through-hole 65 defined at one side thereof, wherein the water-discharge tube 30 of the water discharge assembly or the water-supply hose 26 of the water-supply assembly is connected to the outside via the through-hole 65.

The washstand furniture 10 may further include a frame 70 forming a skeleton between the inner cabinet 40 and the outer cabinet 60. The frame 70 serves to minimize the transfer of the load of the washing device to the cabinet. The frame 70 provides a means of connection between the inner cabinet 40 and the outer cabinet 60.

The inner cabinet 40 accommodates the functional-modules therein. The functional-module may be a device that is housed in the cabinet and operates electrically. The cabinet may house multiple functional-modules.

The washstand furniture 10 may include a first functional-module 100 and a second functional-module 200, both being disposed within the inner cabinet 40. The first functional-module 100 may be disposed at a lower region of the inner cabinet 40 and the second functional-module 200 may be disposed at an upper region of the inner cabinet 40. The first and second functional-modules 100, 200 may configured as drawer units, and hence, may also be referred to herein as a first/second heated drawer assembly.

The washstand furniture 10 may further include a third functional-module 210 disposed between the inner cabinet 40 and the bowl portion 22. The third functional-module 210 may include a water-purification filter 27 for purifying the water supplied to the water-supply assembly and/or a printed circuit board for controlling power supplied to and/or operations of the air-conditioning device 80 or a plurality of functional-modules.

The washstand furniture 10 may include a partition block 50 that divides the spaces that accommodate a plurality of functional-modules of the inner cabinet 40 from one another. The partition block 50 separates the spaces that accommodate the plurality of functional-modules within the inner cabinet 40 from each other. The interior of the inner cabinet 40 may be divided into an upper portion and a lower portion by the partition 50, the upper portion accommodating the second functional-module 200 therein, and the lower portion accommodating the first functional-module 100 therein. Further, in the partition block 50, electrical wiring for supplying power to a functional-module moving forward within the cabinet is disposed.

In the inner side face (or surface) of the inner cabinet 40, a rail member 52 necessary to move the functional-modules 100 and 200 inside or outside the inner cabinet 40 may be disposed. The first functional module 100 or the second functional module 200 may be pulled forward toward the front of the inner cabinet 40 along the rail member 52 disposed in the inner cabinet 40.

Between the inner cabinet 40 and the outer cabinet 60, the external connection path 68 may be defined. The external connection path 68 communicates with the outside air of washstand furniture 10. The external connection path 68 is formed between the rear face 44 of the inner cabinet 40 and the rear outer cabinet wall 64. The external connection path 68 may have a prescribed shape to form a recess or channel at the rear portion inside the cabinet 40 that allows air to flow throughout different spaces inside the cabinet 40. The bottom portion of the external connection path 68 may be opened and communicates with the outside of the washstand furniture 10. The external connection path 68 opens toward the bathroom floor. The external connection path 68 flows air discharged from the first functional module 100 toward the bathroom floor.

A lower portion of the external connection path 68 may be provided with a support member 69 (or support, bracket) that allows spacing between the rear face 44 of the inner cabinet 40 and the rear outer cabinet 64. The support member 69 may be formed in a grid shape so that the external connection path 68 may be in communication with the outside of the washstand furniture 10 while also reinforcing the rigidity of the washstand furniture 10. The support member 69 may be disposed in the lower portion of the external connection path 68 to prevent foreign materials from entering the external connection path 68.

The base outer cabinet 66 disposed below the external connection path 68 has a plurality of holes defined therein for air flow between the external connection path 68 and washstand furniture 10. The frame 70 disposed below the external connection path 68 may also have a plurality of holes defined therein for air flow between the external connection path 68 and washstand furniture 10.

The inner cabinet 40 may have air communication holes 48 and 49 defined at least on one side thereof so that air inside the functional module received therein flows out of the inner cabinet 40. The inner cabinet 40 according to the present embodiment has air-communication holes 48b, 49a, and 49b defined in its rear face 44 for communicating the interior of the functional-module with the external connection path 68. The air-communication holes may include air-inlet holes 48a and 48b through which air flows into the respective functional module, and air-outlet holes 49a and 49b through which air inside respective functional module is discharged to the outside.

The inner cabinet 40 may have air-inlet holes 48a, 48b or air-outlet holes 49a, 49b defined in its bottom face 46 and/or rear face 44. The inner cabinet 40 according to the present embodiment has an air-outlet hole 49a for the first functional-module 100, an air-inlet hole 48b and an air-outlet hole 49b for the second functional-module 200, as defined in the rear face 44 thereof. The inner cabinet 40 according to the present embodiment has an air-inlet hole 48a for the first functional-module 100, defined in its bottom face 46.

The air-communication holes 48b, 49a, 49b defined in the rear face 44 of the inner cabinet 40 act to allow the inside of the inner cabinet 40 to be in communication with the external connection path 68 for air flow.

Between the bottom face 46 of the inner cabinet 40 and the base outer cabinet 66, a containment space is defined to accommodate the air-conditioning device 80. The bottom portion 46 of the inner cabinet 40 may be formed in a stepped fashion so as to define a receiving space for receiving the air-conditioning device 80 in a lower portion thereof. In the stepped portion, there is defined an air-communication hole 48a through which air may be introduced.

The washstand furniture 10 may include an upper cover 72 disposed between the bowl portion 22 of the washstand furniture and the cabinet for primarily to receive water falling from the bowl portion 22. The upper cover 72 allows connection between the bowl portion 22 and the cabinet. The washstand furniture 10 may include an input unit 74 for inputting user commands for operating a plurality of functional-modules and/or the air-conditioning device 80. The input unit 74 may be disposed on one side of the upper cover 72.

The input unit 74 may include a button switch, a membrane switch or a touch panel for receiving operational commands for the functional module or the air-conditioning device 80. The input unit 74 may include a remote controller that receives operation and operation commands for the air-conditioning device 80 or the functional-module and displays operation information. The input unit 74 may include only a power button (not shown) that is activated to power the air-conditioning device 80 or the functional-module.

The washstand furniture 10 may include washstand furniture legs 76 (or support) that space the cabinet from the floor of the bathroom by a predetermined distance. By raising the cabinet 40 of the washstand furniture 10 from the floor, air may be discharged onto the floor and may also allow natural ventilation to prevent mold and fungus growth.

The air-conditioning device 80 may discharge air so as to dehumidify the bottom of the bathroom or to dry the inside of the functional module disposed inside the cabinet. The air-conditioning device 80 may use a fan 94 to discharge air to the first air-outlet 86, which face the bathroom floor, or to the second air-outlet 88, which leads into the cabinet.

The air-conditioning device 80 may be disposed in the lower portion of the inner cabinet 40. The air-conditioning device 80 may also discharge air into the cabinet. The air-conditioning device 80 discharges air to the first functional-module 100 disposed within the cabinet in the lower portion thereof. The air-conditioning device 80 may be disposed below the bottom face of the inner cabinet 40. The air-conditioning device 80 may be spaced apart from the bottom surface of the bathroom by a predetermined distance. The air-conditioning device 80 may be spaced at a certain distance from the bottom surface of the bathroom and discharges air toward the bottom surface of the bathroom. The air-conditioning device 80 may be disposed between the bottom face of the inner cabinet 40 and the base outer cabinet 66. A portion of the housing 82 of the air-conditioning device 80 protrudes into a lower portion of the base outer cabinet 66. The air-conditioning device 80 may be mounted to the base outer cabinet 66.

The air-conditioning device 80 may include the housing 82 which has an air-intake hole 84 defined therein, a first air-outlet 86 used to dry the floor, and a second air-outlet 88 used to dry the interior of the functional-module disposed within the cabinet, as defined therein. The air-conditioning device 80 may include a fan 94 disposed inside the housing 82 to flow air from the air-intake hole 84 to the first air-outlet 86 or the second air-outlet 88; and an air-vane 90 for discharging air flowing inside the housing 82 to the first air outlet 86 or the second air outlet 88. The air-conditioning device 80 may include a heater 92 for heating the air flowing inside the air-conditioning device 80. The air-conditioning device 80 further includes a filter for filtering air sucked into the air-intake hole 84 of the housing 82. The housing 82 may define the contour of the air-conditioning device 80. The housing 82 may be fastened to the cabinet. The housing 82 includes a plurality of fasteners 136 for fastening the housing to a bottom face of the inner cabinet 40 or the base outer cabinet 66.

The air-vane 90 opens and closes the first air-outlet 86 or the second air-outlet 88. The air-vane 90 may be operated by an air-vane drive motor. By the operation of the air-vane drive motor, the first air-outlet 86 or the second air-outlet 88 is opened and closed. Via the operation of the air-vane 90, the first air-outlet 86 and the second air-outlet 88 are selectively opened and closed. When the first air-outlet 86 is opened, the second air-outlet 88 is closed, while when the first air-outlet 86 is closed, the second air-outlet 88 is opened. It is also possible to open both air-outlets 86 and 88.

The fan 94 may generate airflow such that the external air is sucked into the air-intake hole 84 and the air is discharged to the first air-outlet 86 or the second air-outlet 88. The air-intake hole 84 of the air-conditioning device 80 opens toward the bottom of the bathroom. Accordingly, when the fan 94 of the air-conditioning device 80 is operated, the air on the bottom of the bathroom flows to the air-intake hole 84, resulting in a dehumidifying effect due to air convection on the bottom of the bathroom.

The fan 94 may be a cross-flow fan or another appropriate type of fan capable of sucking air from the air-intake hole 84 defined in the rear side of the lower portion of the housing 82 and discharging air toward the air-outlet formed in the front of the housing.

Hereinafter, with reference to FIG. 6 to FIG. 7, the operation mode of the air-conditioning device 80 will be described. The air-conditioning device 80 may operate in a bottom dehumidifying mode for dehumidifying the bottom of the bathroom, or a functional-module drying mode for drying the interior of a functional-module disposed in the cabinet. The air-conditioning device 80 may selectively open the first air-outlet 86 or the second air-outlet 88 via the operation of the air-vane 90. The air-conditioning device 80 may selectively open and close the first air-outlet 86 and the second air-outlet 88 according to the selected operation mode.

The air-conditioning device 80, in the bottom dehumidifying mode, opens the first air-outlet 86 and closes the second air-outlet 88. The air-conditioning device 80, in the bottom dehumidifying mode, allows the air-vane 90 to be oriented as shown in FIG. 5.

In the bottom dehumidifying mode, the air-conditioning device 80 discharges air to the first air-outlet 86. In the bottom dehumidifying mode, via the operation of the heater 92 and the fan 94, warm air may flow in a forced convection manner toward the floor of the bathroom, thereby drying the floor and other low lying regions where moisture may be common.

The heater 92 may be embodied as a PTC (Positive Temperature Coefficient Resistance) heater with a self-temperature sensing function, by which an appropriate temperature is achieved based on the settings of all requirements upon receiving the power, and thus, a separate control device may not be necessary. The heater 92 may be arranged so as to occupy only a portion of a cross-section of a flow path formed in the housing 82, thereby minimizing the flow path resistance.

Figure 6:
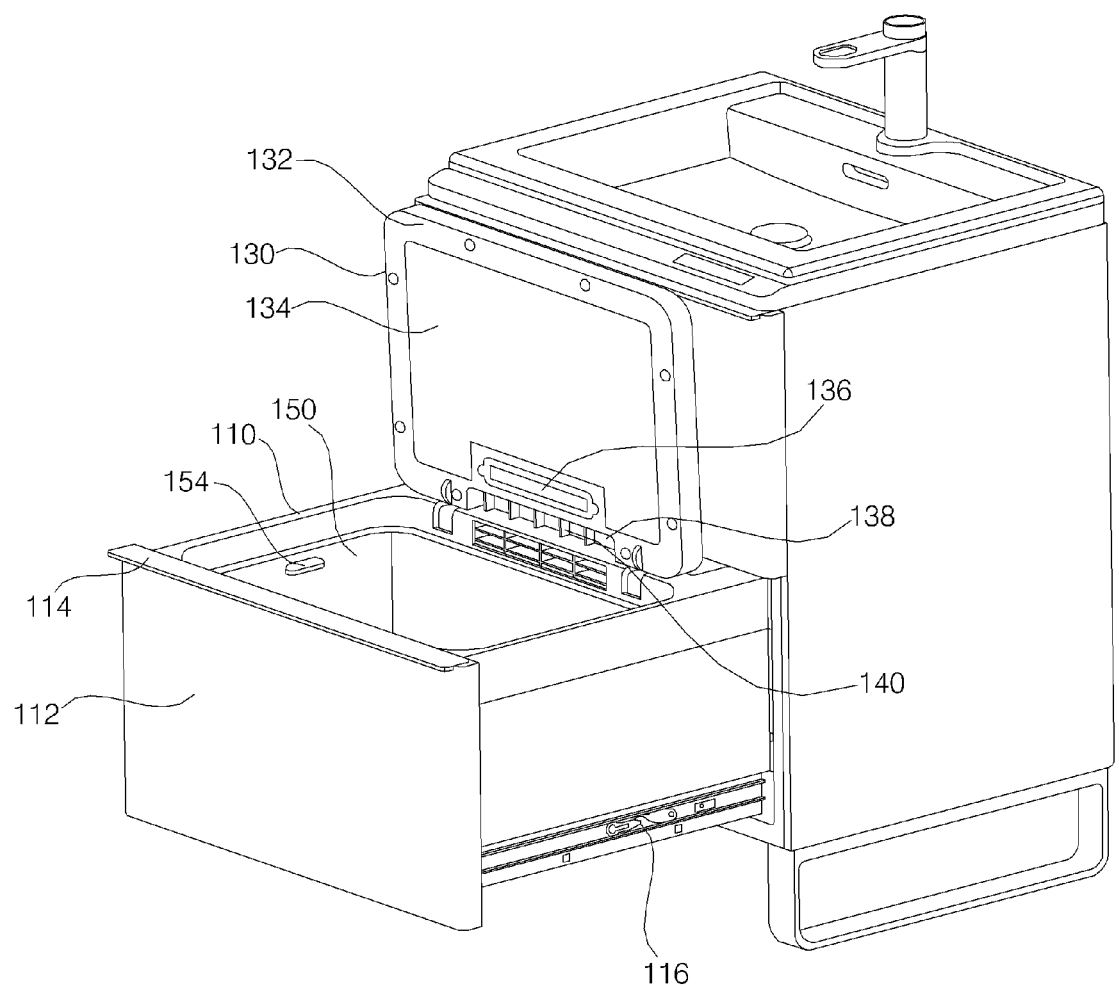
FIG. 6 is a diagram illustrating a state in which the first functional module is opened according to an embodiment of the present disclosure.
Figure 7:
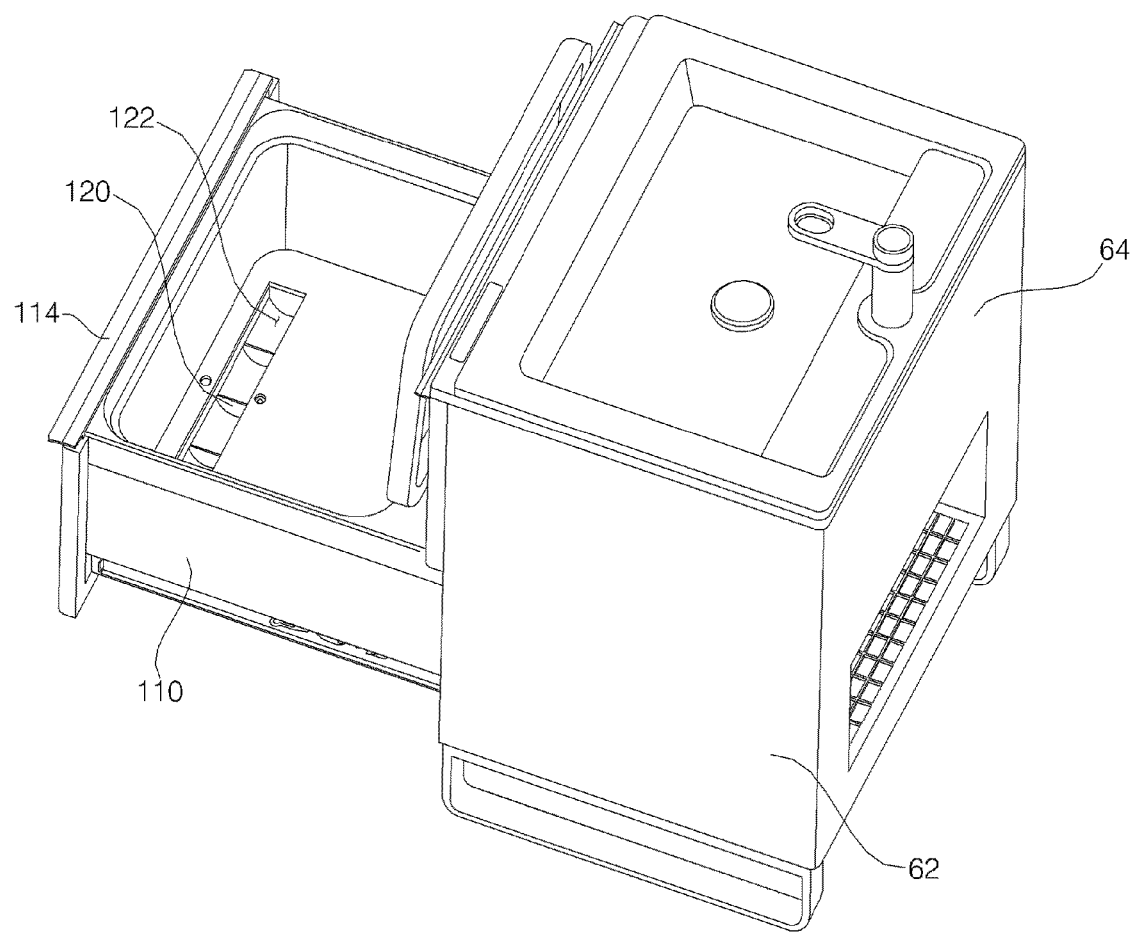
FIG. 7 shows a state in which a basket and a rack are removed from the first functional-module in FIG. 6.
Figure 8:
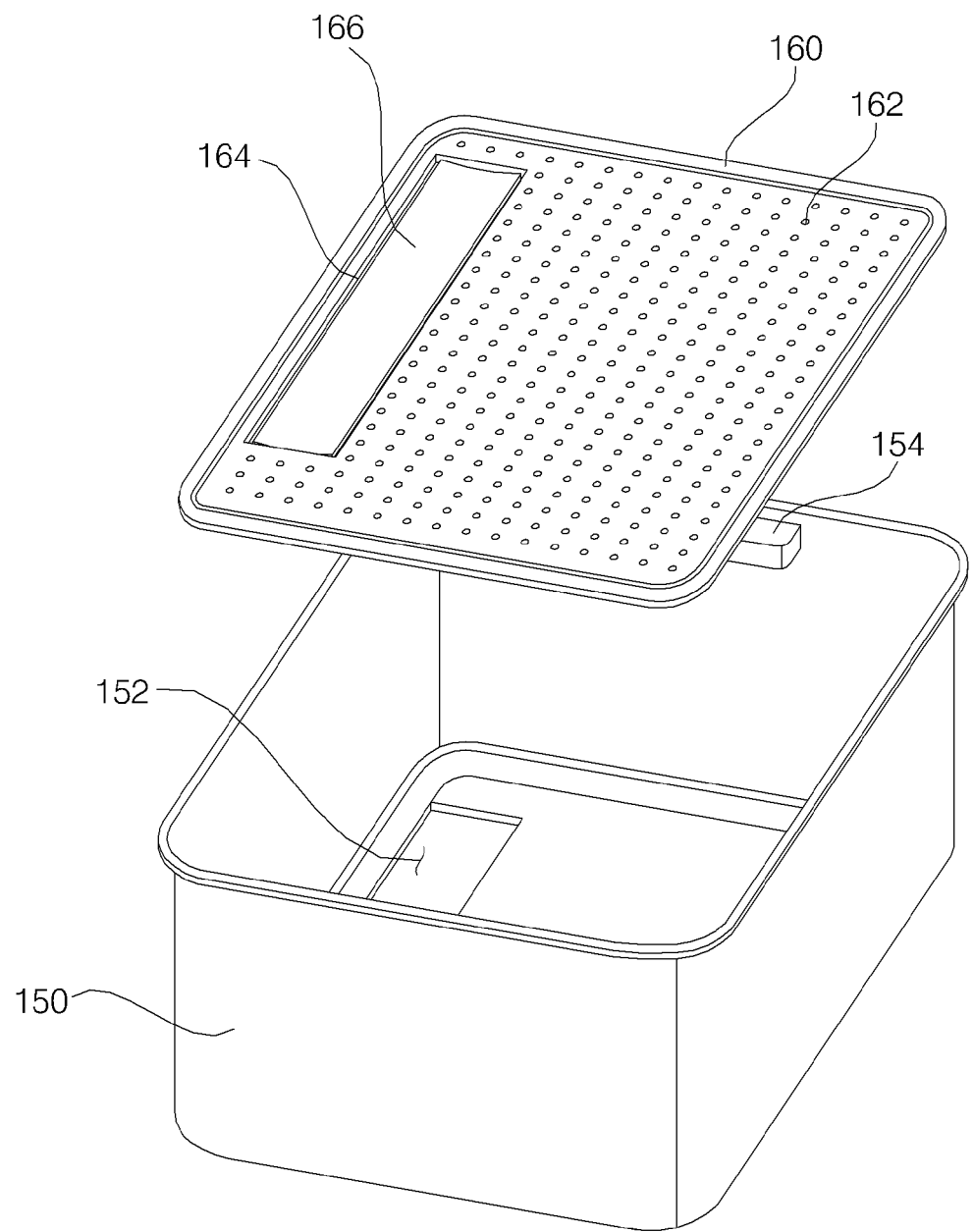
FIG. 8 is a view showing a state in which a basket and a rack are separated according to an embodiment of the present disclosure.
Figure 9:
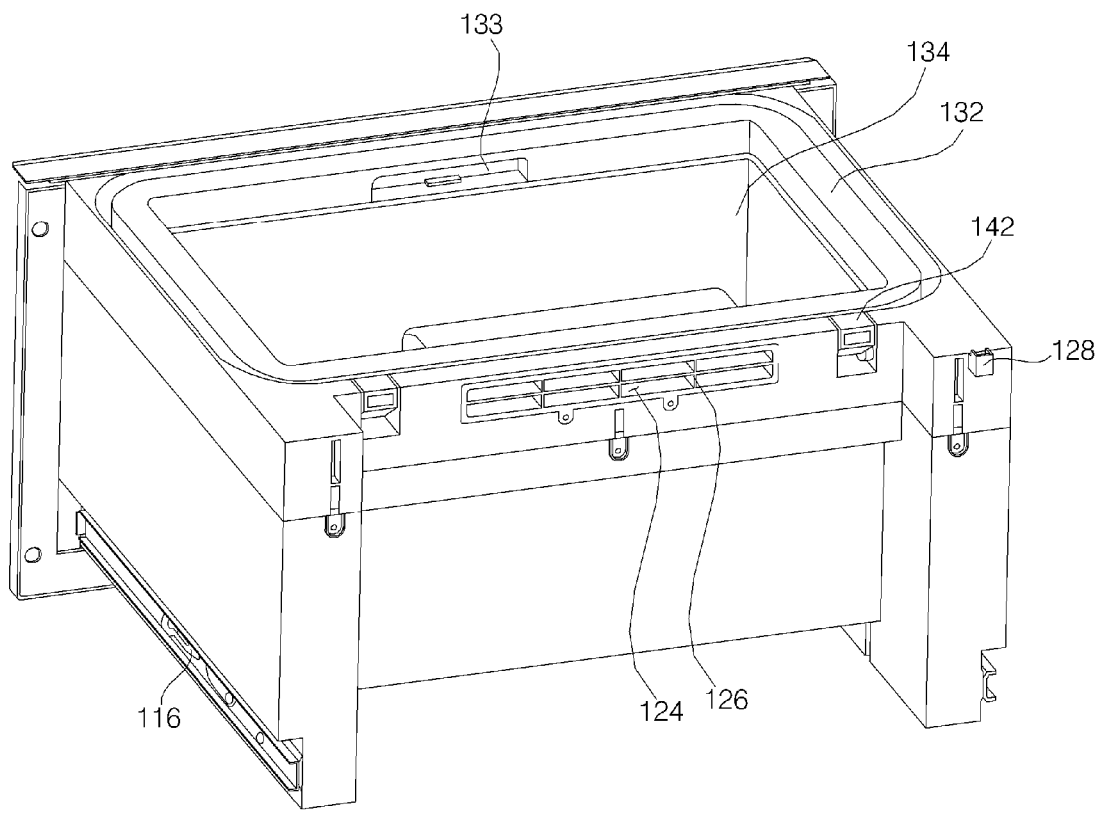
FIG. 9 is a rear perspective view of the first functional module according to an embodiment of the present disclosure.
Figure 10:
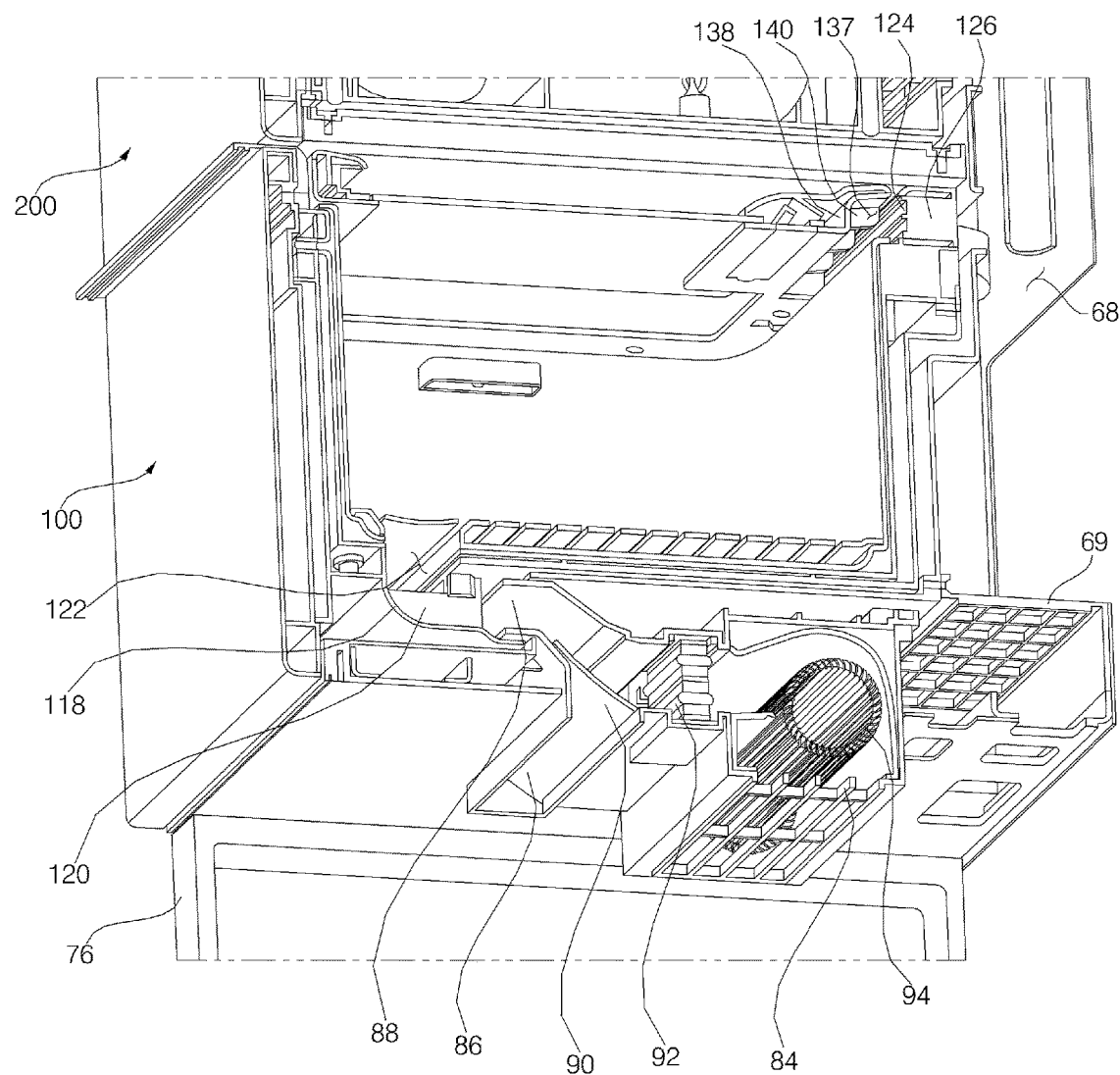
FIG. 10 is a view illustrating the connection relationship between the air-conditioning device and the first functional module of washstand furniture according to an embodiment of the present disclosure.

FIG. 6 is a diagram illustrating a state in which the first functional module is opened according to an embodiment of the present disclosure. FIG. 7 shows a state in which a basket and a rack are removed from the first functional-module of FIG. 6. FIG. 8 is a view showing a state in which a basket and a rack are separated according to an embodiment of the present disclosure. FIG. 9 is a rear perspective view of the first functional module according to an embodiment of the present disclosure. FIG. 10 is a view illustrating the connection relationship between the air-conditioning device and the first functional module of washstand furniture according to an embodiment of the present disclosure.

The first functional-module 100 (or 'utensil drying functional-module' or 'heated drawer assembly') may be configured to dry utensils and various other items that are used in the bathroom. The first functional-module 100 may use hot air blown from the air-conditioning device 80 to dry the utensils. The utensils used in the bathroom may include all kinds of utensils that may be used in the bathroom.

The first functional module 100 may include a drawer 110 having a space therein for accommodating utensils inside the inner cabinet 40 and may be configured to move between the interior of the cabinet and the front of the cabinet, and a rack 160 disposed within the drawer 110 to hold the utensils.

The first functional module 100 may further include a basket 150 detachably disposed within the drawer 110. The drawer 110 may be hollow with an open top. The basket 150 may be inserted into the opened top of the drawer 110. The rack 160 may be placed inside the basket 150.

The first functional-module 100 may further include an air-inlet member 118 (or air inlet, connection duct) having therein an inlet passage 122 in communication with the air-conditioning device 80, and an air-outlet member 126 (or grill) having an air-outlet defined therein to allow air inside the first functional-module 100 to be discharged outside the first functional-module 100.

The first functional module 100 may include a front portion 112 disposed in front of the drawer 110 and a drawer handle 114 projected forward from the top of the front portion 112. The front portion 112 may be disposed at a front position of washstand furniture 10. With the drawer 110 being inserted into the cabinet, the front portion 112 may cover the front of the cabinet. The drawer handle 114 may be projected forward so that the user may pull the functional-module in a front direction of the cabinet using the handle.

The drawer 110 may have a box shape in which the inside is hollow and the top is opened. At the opened top of the drawer 110, a door 130 for opening and closing the top of the drawer 110 may be disposed. The door 130 may be hinge-coupled to the top of the drawer 110. The door 130 opens and closes the open top portion of the drawer 110. When the top of the drawer 110 is opened, the user may take the basket 150 out of the drawer 110 or insert the basket 150 into the drawer 110.

The first functional module 100 may further include a hinge-assembly 142 for pivoting the door 130 to open or close the top of the drawer 110. The hinge-assembly 142 pivots the door 130 so that the door 130 opens and closes the drawer 110. The hinge-assembly 142 is configured such that the wiring is passed there-through. Thus, the wiring disposed inside the drawer 110 may be connected to the ultraviolet lamp 136 disposed on the door 130. When the door 130 is opened, the basket 150 may be inserted into the drawer 110 or the basket 150 may be taken out of the drawer 110.

The door 130 may include a blocking portion 134 for shielding the opened top of the drawer 110 and an edge portion 132 for sealing the top of the drawer 110 along the periphery of the blocking portion 134. The blocking portion 134 may be formed of a transparent material so that the user can visually check the interior of the drawer 110. The blocking portion 134 may be made of transparent glass or plastic.

The door 130 may be described herein via the following spatial definitions. When the door 130 is closed, the side located inside the drawer 110 is defined as the inner side, and the side located outside the drawer 110 is defined as the outer side. This definition is merely for facilitating the description of the present disclosure, and are not intended to limit the present disclosure.

The door 130 has a door handle 133 on its outer side, which may be used to open and close the door 130. The door handle 133 may be formed on an outer side of the edge portion 132.

The door 130 has an air-outlet communication groove 138 defined in a portion adjacent to the air-outlet member 126, such that the air inside the first functional-module 100 flows to the air-outlet 124 (or opening/hole). The air-outlet communication groove 138 may be recessed into the edge portion 132 at a portion adjacent to the air-outlet member 126 so that the air inside the first functional-module 100 flows into the air-outlet 124 of the air-outlet member 126, thereby to define an air-outlet communication channel 137.

The edge portion 132 may include an air-outlet communication groove-support member 140 (or support) that maintains the rigidity of the edge portion 132 at the portion where the air-outlet communication groove 138 is formed. The plurality of air-outlet communication groove-support members 140 may be arranged in parallel to a direction of the air-outlet 124. The air-outlet communication groove-support member 140 may guide the air in the air-outlet communication channel 137 to the air-outlet 124.

The door 130 may further include an ultraviolet lamp that sterilizes the utensil disposed within the drawer 110. The ultraviolet lamp is disposed inside the door 130. Inside the edge portion 132, the ultraviolet lamp 136 for disinfecting the utensils contained in the drawer 110 may be disposed.

The first functional module 100 may include a movable member 116 (or rail, slide) to allow inserting of the drawer 110 into or out of the cabinet. The movable member 116 may be disposed on the side face of the drawer 110. The movable member 116 moves along the rail member 52 (or rail, slide) of the inner cabinet 40. As the movable member 116 of the drawer 110 moves along the rail member 52 of the inner cabinet 40, the drawer 110 is inserted into the inner cabinet 40 or drawn out in a front direction of the inner cabinet 40.

The drawer 110 may include a wire connection member 128 (or wire connection harness) that acts to connect wirings from the cabinet or the partition 50 to the inside of the drawer 110. The wire connection member 128 protrudes from one side of the drawer 110 in a direction of the cabinet or the partition 50. The wire connection member 128 may protrude from the rear of the drawer 110 and may be bent in the direction of the partition 50.

The electrical wires may be connected into the drawer 110 via the wire connection member 128. The wiring connected to the inside of the drawer 110 via the wire connection member 128 may be connected to the ultraviolet lamp 136 as described below. The wiring connected via the wire connection member 128 may pass through the hinge-assembly 142, then pass through the edge portion 132 of the door 130, and, in turn, may be connected to the ultraviolet lamp 136.

The drawer 110 may include an air-inlet member 118 that allows air drawn from the air-conditioning device 80 to flow into the drawer 110. The air-inlet member 118 may be disposed in the lower portion of the drawer 110. The air-inlet member 118 allows the warm air discharged from the air-conditioning device 80 to flow into the first functional-module 100. One end of the air-inlet member 118 may be air-communicated with the air-outlet of the air-conditioning device 80. The air-inlet member 118 may have a prescribed shape that extends down from a bottom of the first functional-module 84 and toward the rear to be coupled to the air conditioning device 80. The air-inlet member 118 having the prescribed shape may form an air channel or duct to guide air into the drawer 110.

The air-inlet member 118 may form an inlet passage 122 defined therein for guiding air discharged from the air-conditioning device 80 to the first functional-module 100. Within the air-inlet member 118, an inlet passage-support member 120 supporting the inlet passage 122 is disposed. The inlet passage-support member 120 (or flow guide) may guide air flowing within the inlet passage 122.

The air-inlet member 118 may be removably coupled with the dryer 80. With the drawer 110 being inserted into the cabinet, the air-inlet member 118 may be connected to the air-conditioning device 80. Specifically, as shown in FIG. 3, a portion of the housing 82 of the air-conditioning device 80 defining the second air-outlet 88 passes through the air-communication hole 48a of the inner cabinet 40, and then is inserted into the inlet passage 122 of the air-inlet member 118. When the drawer 110 is pulled out, the air-inlet member 118 and the housing 82 may separate from each other to allow the drawer 110 to be opened.

The inlet passage 122 defined at the end of the air-inlet member 118 may be formed parallel to the direction in which the drawer 110 moves by the movable member 116. The inlet passage 122 communicates with the air-conditioning device 80, along with the drawer 110 being inserted into the inner cabinet 40.

The drawer 110 may include an air-outlet member 126 (or grill) having an air-outlet 124 defined therein such that the air inside the functional-module is vented outside the functional-module. The air-outlet member 126 is shown as being separate from the drawer 110, but the present disclosure is not limited thereto. The air-outlet member 126 may be formed integrally with the drawer 110.

The air-outlet member 126 may be disposed in the upper portion of the drawer 110. The air-outlet member 126 may be formed at a position corresponding to the air-communication hole 49a formed in the inner cabinet 40. The air-outlet member 126 may be disposed in the rear upper portion of the drawer 110. The air-outlet member 126 may be disposed at a level higher than the level of the basket 150 accommodated in the drawer 110. The air-outlet member 126 may be disposed at a position corresponding to the door 130 of the drawer 110. Referring to FIG. 10, the air-outlet member 126 may be disposed at the same height as the portion where the door 130 is disposed. In the portion where the air-outlet member 126 is disposed, the door 130 has an inwardly-extending air-outlet communication channel 137 so that the air inside the functional-module may flow to the air-outlet 124.

The basket 150 is accommodated in the drawer 110. The basket 150 may be inserted into the drawer 110 through the open top of the drawer 110, or drawn out of the drawer 110 through the open top of the drawer 110. The basket 150 may have a hollow interior and an open top. The basket 150 may have a space defined therein for accommodating the utensils to be dried therein.

The basket 150 may have a bottom hole 152 defined in part of the bottom. The bottom hole 152 communicates with the inlet passage 122 inside the air-inlet member 118. Air discharged from the air-conditioning device 80 flows into the basket 150 through the inlet passage 122 and the bottom hole 152.

The basket 150 may have a basket handle 154 protruding inwardly from one side thereof. The user may pull the basket 150 from the drawer 110 using the handle 154 of the basket 150.

The rack 160 may be provide to hold utensils or various other items. The rack 160 may be placed inside the basket 150 to deliver water falling from the utensils to the bottom of the basket 150. The rack 160 may be spaced at a certain distance from the bottom of the basket 150.

The rack 160 may be disposed in a lower portion of the basket 150. The rack 160 may have a plurality of water transfer holes 162 that serve to deliver water falling away from the utensil disposed within the basket 150 to the bottom surface of the basket 150. The rack 160 may have a plurality of water transfer holes 162 for water-communicating between an upper portion thereof where the utensil is held and a lower portion facing the bottom surface of the basket 150.

The rack 160 may have an air-flow hole 164 defined in a portion corresponding to the position where the bottom hole 152 of the basket 150 is formed. The air-flow hole 164 communicates with the inlet passage 122 inside the air-inlet member 118 of the drawer 110. Air discharged from the air-conditioning device 80 flows into the basket 150 through the air-flow hole 164 of the rack 160. The warm air that enters the basket 150 dries the utensil held in the rack 160.

The rack 160 may include an air-flow hole cover 166 that covers the air-flow hole 164. The air-flow hole cover 166 is disposed at an upper position of the rack, where the air-flow hole 164 is formed. The air-flow hole cover 166 prevents the utensils held in the rack 160 from falling into the inlet passage 122 through the air-flow hole 164.

Figure 11A:
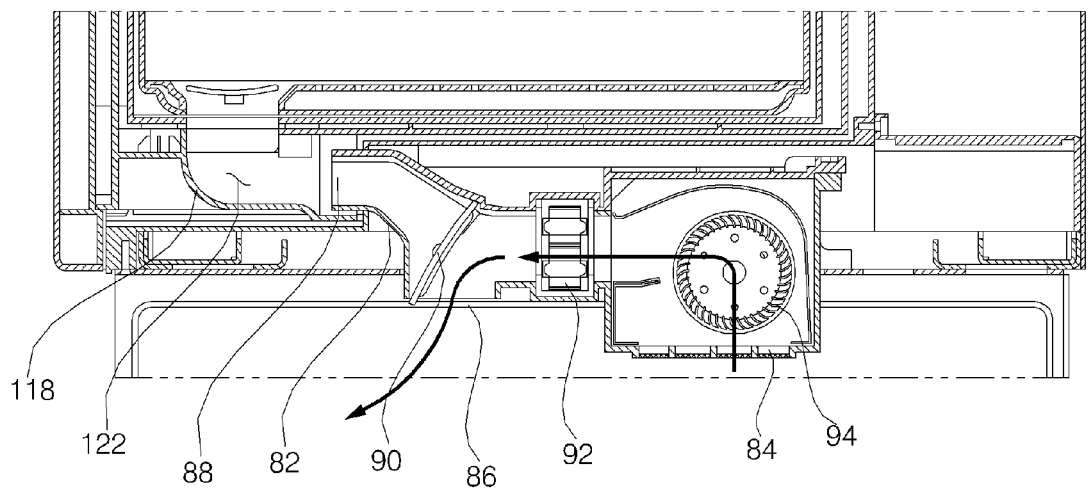
FIG. 11A is a diagram illustrating an air flow when the air-conditioning device according to an embodiment of the present disclosure is in the bottom dehumidification mode.
Figure 11B:
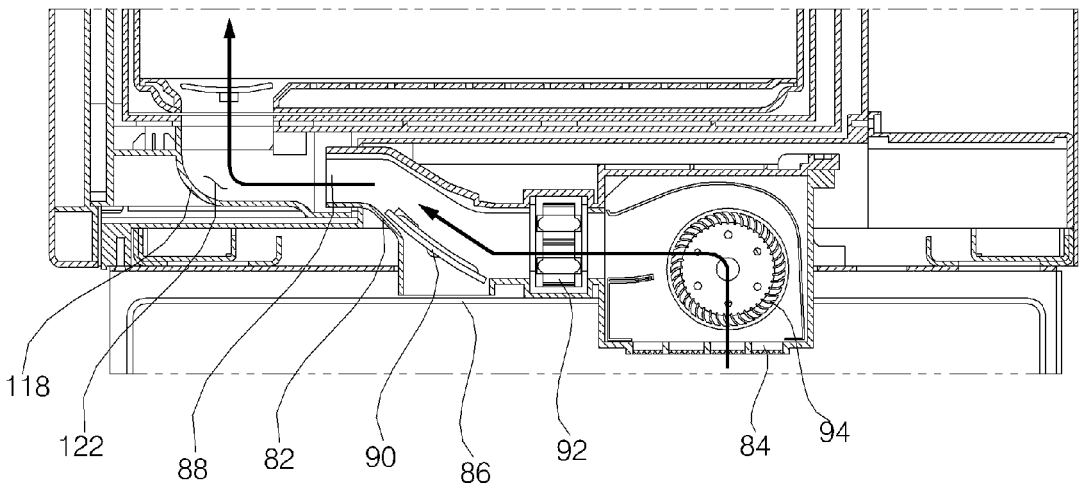
FIG. 11B is a diagram illustrating air-flow when the air-conditioning device according to an embodiment of the present disclosure is in a functional-module drying mode.
Figure 12:
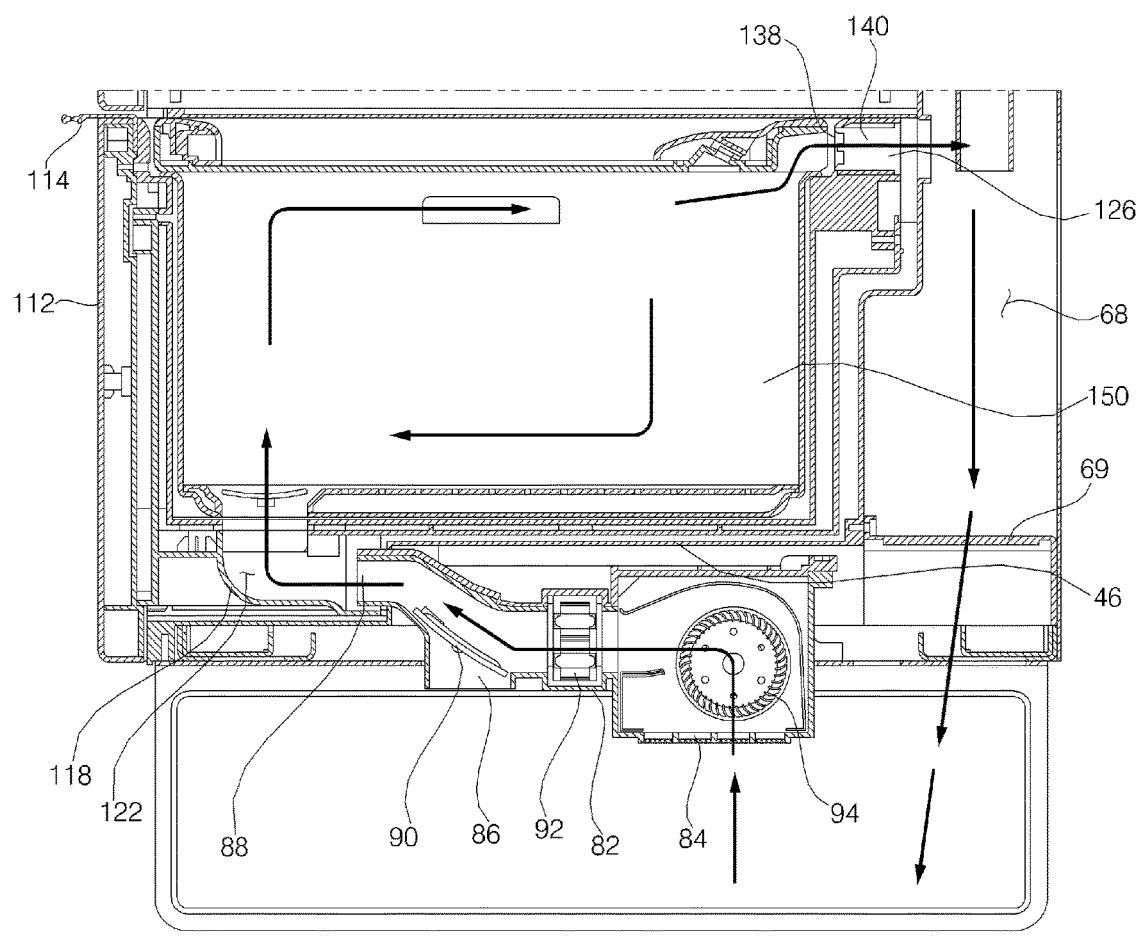
FIG. 12 is a diagram illustrating air-flow in the first functional-module according to the operation of the air-conditioning device in FIG. 11B.

FIG. 11A is a diagram illustrating an air flow when the air-conditioning device is in the bottom dehumidification mode. FIG. 11B is a diagram illustrating air-flow when the air-conditioning device is in a functional-module drying mode. FIG. 12 is a diagram illustrating air-flow in the first functional-module according to the operation of the air-conditioning device in FIG. 11B.

Hereinafter, referring to FIG. 11 to FIG. 12, the flow of air via the orientation of the air-vane of the air-conditioning device, and the flow of air within the washstand furniture 10 when air flows into the first functional-module will be described.

The air-conditioning device 80 may operate in a bottom dehumidifying mode for dehumidifying the floor of the bathroom, or a functional-module drying mode for drying the interior of the functional module disposed in the cabinet. The air-conditioning device 80 may selectively open the first air-outlet 86 or the second air-outlet 99 via the operation of the air-vane 90. In other words, the air-conditioning device 80 may selectively open or close the first air-outlet 86 and the second air-outlet 88 depending on the selected operation mode.

The air-conditioning device 80, in the bottom dehumidifying mode, opens the first air-outlet 86 and closes the second air-outlet 88. The air-conditioning device 80, in the bottom dehumidifying mode, allows the air-vane 90 to be oriented as shown in FIG. 11A.

In the bottom dehumidifying mode, the air-conditioning device 80 discharges air to the first air-outlet 86. In the bottom dehumidifying mode, via the operation of the heater 92 and the fan 94, warm air may flow in a forced convection manner to the floor of the bathroom, thereby drying the floor.

The air-conditioning device 80, in the functional-module drying mode, opens the second air-outlet 88 and closes the first air-outlet 86. In the functional-module drying mode, the air-conditioning device 80 allows the air-vane 90 to be oriented as shown in FIG. 11B.

In functional-module drying mode, the air-conditioning device 80 discharges air to the second air-outlet 88. In the functional-module drying mode, the air-conditioning device 80 may operate the heater 92 and the fan 94 to dry the interior of the functional-module by discharging warm air into the functional-module.

More specifically, with reference to FIG. 12, in the functional-module drying mode, the air-conditioning device 80 directs the air-vane 90 to open the second air-outlet 88. The air-conditioning device 80 sucks air through the air-intake hole 84 that opens toward the bottom of the bathroom. The air-conditioning device 80 may generate airflow in a convection manner using ambient air on the bathroom floor surface during the suction of air through the air-intake hole 84, thereby to dry the bathroom floor around the air-intake hole.

The air-conditioning device 80 operates the heater 92 and the fan 94 to discharge the heated air into the first functional-module 100. The inlet passage 122 guides the air discharged from the second air-outlet 88 into the first functional-module 100. The warm air introduced into the first functional-module 100 may flow across the interior of the first functional-module 100 and dries the utensils held therein. The warm air flowing inside the first functional-module 100 may upward in the first functional-module 100. The air flowing upwards inside the first functional-module 100 flows into the air-outlet 124 defined in the upper region of the drawer 110. The air-outlet communication channel 137 defined in one side of the door 130 directs the upwardly-flowing air to the air-outlet member 126 having the air-outlet 124 defined therein.

The air that has flowed into the upper position of the drawer 110 may flow through the air-outlet 124 into the external connection path 68. In the first functional module 100, the air introduced into the external connection path 68 may be discharged downward through the lower open portion of the external connection path 68. The lower portion of the external connection path 68 may be open toward the bottom surface of the bathroom, and thus the air exiting through the external connection path 68 may dry the floor in the bathroom.

Embodiments of the present disclosure are to provide washstand furniture to be able to dry a utensil used in a bathroom.

Embodiments of the present disclosure are to provide washstand furniture to recycle waste heat coming from warm air used in utensil drying process.

Embodiments of the present disclosure are to provide washstand furniture that effectively dries an inner portion of a functional-module.

The purposes of the present disclosure are not limited to the above-mentioned purposes. Other purposes as not mentioned herein may be clearly understood by those skilled in the art from the following description.

In a first aspect of the present disclosure, there is provided a washstand furniture which may comprise: a washing device including: a bowl portion; a water-supply assembly for supplying water to the bowl portion; and a water-discharge assembly for discharging water from the bowl portion; an inner cabinet disposed below the bowl portion and having an inner space defined therein; an air-conditioning device configured to draw air through an air-intake hole opened toward a bathroom floor and to discharge air into the inner space of the inner cabinet; an utensil drying functional-module disposed in the inner space of the inner cabinet and configured to dry utensils held therein using air discharged from the air-conditioning device; and an outer cabinet covering an outer side of the inner cabinet, wherein an external connection path is defined between the inner cabinet and the outer cabinet, wherein the external connection path guides air discharged from the utensil drying functional-module toward the bathroom bottom.

In one implementation of the first aspect, the washstand furniture may further include an air-inlet member disposed below the utensil drying functional module, wherein the air-inlet member has an inlet passage defined therein to guide air ejected from the air-conditioning device into the utensil drying functional-module.

In one implementation of the first aspect, the utensil drying functional-module may include an air-outlet member having an air-outlet defined therein to air-communicate an inner space of the utensil drying functional-module with the external connection path.

In one implementation of the first aspect, the inner cabinet may have an air-communication hole defined therein to allow flow of air in the utensil drying functional module into the external connection path.

In one implementation of the first aspect, the air-communication hole may be defined at a position corresponding to the air-outlet member.

In one implementation of the first aspect, the utensil drying functional-module may include: a drawer configured to move in the inner cabinet and to have a space therein for accommodating utensils therein; and a rack disposed within the drawer for holding the utensils, wherein the air-outlet member is disposed in an upper portion of the drawer.

In one implementation of the first aspect, the utensil drying functional-module may further comprise a door to open or close an opened top of the drawer, wherein the air-outlet member is disposed at a position corresponding to the door, wherein the door has an air-outlet communication channel defined therein for guiding air inside the utensil drying functional-module to the air-outlet.

In one implementation of the first aspect, the washstand furniture may further comprise an air-inlet member disposed below the drawer, wherein the air-inlet member has an inlet passage defined therein to guide air discharged from the air-conditioning device into the utensil drying functional-module, wherein when the drawer is inserted into the inner cabinet, the inlet passage air-communicates with the air-conditioning device.

In one implementation of the first aspect, the air-conditioning device may further include a heater for heating air to be discharged into the inner space formed in the inner cabinet.

In one implementation of the first aspect, the outer cabinet may include: lateral outer cabinets respectively covering both side faces of the inner cabinet; a rear outer cabinet covering a rear face of the inner cabinet; and a base outer cabinet covering a bottom face of the inner cabinet, wherein the external connection path is defined between the rear outer cabinet and a rear face of the inner cabinet.

In a second aspect of the present disclosure, there is provided a washstand furniture which may comprise: a washing device including: a bowl portion; a water-supply assembly for supplying water to the bowl portion; and a water-discharge assembly for discharging water from the bowl portion; a cabinet disposed below the bowl portion and having an inner space defined therein; an air-conditioning device configured to discharge air into the inner space of the cabinet; and an utensil drying functional-module disposed in the cabinet and configured to dry utensils held therein using air discharged from the air-conditioning device.

In one implementation of the second aspect, the utensil drying functional-module may include: a drawer configured to move into or out of the cabinet and to have a space therein for accommodating utensils therein; and a rack disposed within the drawer for holding the utensils.

In one implementation of the second aspect, the utensil drying functional-module may further include a basket detachably disposed within the drawer, wherein the rack is disposed inside the basket.

In one implementation of the second aspect, the utensil drying functional-module may include: an air-inlet member having an inlet passage defined therein for enabling air-communication between the air-conditioning device and the drawer; and an air-outlet member having an air-outlet defined therein through which air inside the utensil drying functional-module is discharged out of the utensil drying functional-module.

In one implementation of the second aspect, the basket may have a bottom hole defined in a bottom portion thereof communicating with the inlet passage of said air-suctioning member.

In one implementation of the second aspect, the rack may have a plurality of water transfer holes defined therein to deliver water dropped from the utensil to the bottom of the basket.

In one implementation of the second aspect, the rack may have an air-flow hole defined in a portion thereof corresponding to a position where the bottom hole of the basket is formed, wherein the rack has an air-flow hole cover to partially cover the air-flow hole, wherein the air-flow hole cover is disposed in an upper position of the rack.

In one implementation of the second aspect, the air-outlet member may be disposed at a level higher than a level of the basket received in the drawer.

In one implementation of the second aspect, the drawer may be hollow and may have an open top, wherein the utensil drying functional-module includes: a door for opening and closing the open top of the drawer; and an ultraviolet lamp disposed inside the door for sterilizing the utensil held within the drawer.

In one implementation of the second aspect, the utensil drying functional-module may include a door for opening and closing an open top of the drawer, wherein the door may include: a blocking portion for blocking the open top of the drawer; and an edge portion disposed around the blocking portion to seal the open top of the drawer, wherein the edge portion has an air-outlet communication groove recessed into the edge portion at a portion thereof adjacent to the air-outlet member, wherein air in the utensil drying functional module flows into the air-outlet through a space defined by the groove.

The advantages of the present disclosure are not limited to the following:

First, as for the washstand furniture according to the present disclosure, the air discharged by the air-conditioning device flows into the inner cabinet to dry the utensil disposed inside the module. At the same time, the air-conditioning device's air-intake hole and the external connection path as the air discharge channel of the washstand furniture both are opened toward the bathroom floor, thus, the bathroom floor is dried, thereby creating a clean bathroom space.

Second, as for the washstand furniture according to the present disclosure, the inlet passage for the utensil drying functional-module is placed in a lower portion of the utensil drying functional-module, while the air-outlet thereof is placed in an upper portion of the utensil drying functional-module. This allows hot air discharged from the air-conditioning device to move from the bottom to the top thereof to circulate through the utensil drying functional-module, thereby to quickly dry the utensils inside the module.

It will be understood by those skilled in the art that the present disclosure may be embodied in other specific forms without departing from the spirit or essential characteristics thereof. It is therefore to be understood that the above-described embodiments are illustrative and non-restrictive in every respect. The scope of the present disclosure is defined by the appended claims rather than by the foregoing descriptions. All changes or modifications derived from the meaning and scope of the claims and the equivalents thereof should be interpreted to be included in the scope of the present disclosure.

It will be understood that when an element or layer is referred to as being "on" another element or layer, the element or layer can be directly on another element or layer or intervening elements or layers. In contrast, when an element is referred to as being "directly on" another element or layer, there are no intervening elements or layers present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings of the present disclosure.

Spatially relative terms, such as "lower", "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the disclosure are described herein with reference to cross-section illustrations that are schematic illustrations of idealized embodiments (and intermediate structures) of the disclosure. As such, variations from the shapes of the illustrations as a result, for example, of manufacturing techniques and/or tolerances, are to be expected. Thus, embodiments of the disclosure should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Any reference in this specification to "one embodiment," "an embodiment," "example embodiment," etc., means that a particular feature, structure, or characteristic described in connection with the embodiment is included in at least one embodiment. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A washstand furniture comprising:
   a washing device including
     a bowl,
     a water-supply assembly that supplies water to the bowl, and
     a water-discharge assembly that drains water from the bowl;
   an inner cabinet provided below the bowl and having an inner space;
   a dryer configured to draw air through an air-intake hole opened toward a floor and to discharge air into the inner space of the inner cabinet;
   a utensil drying functional-module provided above the dryer and in the inner space of the inner cabinet and configured to provide a utensil s ace to dry utensils therein by using air discharged from the dryer; and
   an outer cabinet covering an outer side of the inner cabinet,
   wherein an external connection path is defined between the inner cabinet and the outer cabinet,
   wherein the external connection path guides air discharged from the utensil drying functional-module toward the floor,
   wherein the dryer further includes a heater that heats air to be discharged into the inner space in the inner cabinet,
   wherein the utensil drying functional-module includes an inlet passage that is opened downward to guide the air discharged from the dryer to the utensil space, and an air-outlet that is opened rearward so that air in the utensil space is discharged to the external connection path, and wherein the external connection path forms a space at the rear of the utensil drying functional-module and opens downward.

2. The washstand furniture of claim 1, further comprising an air-inlet connection duct provided below the utensil drying functional module, wherein the air-inlet connection duct has an inlet passage defined to guide air ejected from the dryer into the utensil drying functional-module.

3. The washstand furniture of claim 1, wherein the utensil drying functional-module includes an air-outlet grill having an air-outlet such that an inner space of the utensil drying functional-module is in communication with the external connection path for air flow.

4. The washstand furniture of claim 3, wherein the inner cabinet has an air-communication hole to allow flow of air in the utensil drying functional module into the external connection path.

5. The washstand furniture of claim 4, wherein the air-communication hole is defined at a position corresponding to the air-outlet grill.

6. The washstand furniture of claim 3, wherein the utensil drying functional-module includes:
a drawer configured to slide in and out of the inner cabinet and to have a space to accommodate utensils; and
a rack provided within the space of the drawer for placing the utensils,
wherein the air-outlet grill is provided in an upper portion of the drawer.

7. The washstand furniture of claim 6, wherein the utensil drying functional-module includes a door to open or close an opened top of the drawer, wherein the air-outlet grill is provided at a position corresponding to the door,
wherein the door has an air-outlet communication channel defined to guide air inside the utensil drying functional-module to the air-outlet.

8. The washstand furniture of claim 6, further comprising an air-inlet connection duct provided below the drawer, wherein the air-inlet connection duct has an inlet passage to guide air discharged from the dryer into the utensil drying functional-module,
wherein when the drawer is inserted into the inner cabinet, the inlet passage communicates with the dryer.

9. The washstand furniture of claim 1, wherein the outer cabinet includes
lateral outer cabinet walls respectively covering both lateral sides of the inner cabinet;
a rear outer cabinet wall that covers a rear side of the inner cabinet; and
a base outer cabinet wall that covers a bottom side of the inner cabinet,
wherein the external connection path is defined between the rear outer cabinet wall and a rear surface of the inner cabinet.

10. A washstand furniture comprising:
a washing device including:
a bowl;
a water-supply assembly that supplies water to the bowl; and
a water-discharge assembly that drains water from the bowl;
a cabinet provided below the bowl and having an inner space;

a dryer configured to discharge air into the inner space of the cabinet; and
a utensil drying functional-module provided in the cabinet and configured to dry utensils using air discharged from the dryer,
wherein the utensil drying functional-module includes:
a drawer configured to slide into or out of the cabinet and to have a space to accommodate the utensils; and
a rack provided within the drawer to receive the utensils,
wherein the drawer includes an inlet passage opened downward to guide the air discharged from the dryer to the space to accommodate the utensils, and an air-outlet opened rearward so that air in the space to accommodate the utensils is discharged to an outside of the drawer,
wherein the rack includes an air-flow hole that connects the inlet passage and the space to accommodate the utensils, and an air-flow hole cover to partially cover the air-flow hole, and
wherein the air-flow hole cover is provided in an upper portion of the rack.

11. The washstand furniture of claim 10, wherein the utensil drying functional-module includes a basket detachably provided in the drawer, wherein the rack is provided inside the basket.

12. The washstand furniture of claim 11, wherein the utensil drying functional-module includes
an air-inlet member having an inlet passage such that the dryer is in communication with the drawer for air flow; and
an air-outlet member having an air-outlet through which air inside the utensil drying functional-module is discharged out of the utensil drying functional-module.

13. The washstand furniture of claim 12, wherein the basket has a bottom hole defined in a bottom portion and in communication with the inlet passage of the air-inlet member.

14. The washstand furniture of claim 13, wherein the air-flow hole is formed on an upper side of the bottom hole of the basket.

15. The washstand furniture of claim 12, wherein the air-outlet member is provided at a height higher than a height of the basket received in the drawer.

16. The washstand furniture of claim 15, wherein the utensil drying functional-module includes a door to open and close an open top of the drawer,
wherein the door includes
a blocking portion that covers the open top of the drawer; and
an edge portion provided around the blocking portion to seal the open top of the drawer,
wherein the edge portion has an air-outlet communication groove recessed into the edge portion at a portion adjacent to the air-outlet member, wherein air in the utensil drying functional module flows into the air-outlet through a space defined by the groove.

17. The washstand furniture of claim 11, wherein the rack has a plurality of water transfer holes to deliver water dropped from the utensils to the bottom of the basket.

18. The washstand furniture of claim 10, wherein the drawer is hollow and has an open top, wherein the utensil drying functional-module includes
a door to open and close the open top of the drawer, and an ultraviolet lamp provided inside the door and configured to sterilize the utensils held within the drawer.

* * * * *